United States Patent
Delhom

(10) Patent No.: US 9,974,736 B2
(45) Date of Patent: May 22, 2018

(54) VETERINARY PHARMACEUTICAL COMPOSITIONS AND METHOD FOR THE PRODUCTION THEREOF

(71) Applicant: VIRBAC, Carros (FR)

(72) Inventor: Nathalie Delhom, Vence (FR)

(73) Assignee: VIRBAC, Carros (FR)

( * ) Notice: Subject to any disclaimer, the term of this patent is extended or adjusted under 35 U.S.C. 154(b) by 126 days.

(21) Appl. No.: 14/655,987

(22) PCT Filed: Dec. 19, 2013

(86) PCT No.: PCT/IB2013/061141
§ 371 (c)(1),
(2) Date: Jun. 26, 2015

(87) PCT Pub. No.: WO2014/102679
PCT Pub. Date: Jul. 3, 2014

(65) Prior Publication Data
US 2015/0335595 A1 Nov. 26, 2015

(30) Foreign Application Priority Data
Dec. 27, 2012 (FR) .................................... 12 62821

(51) Int. Cl.
| | |
|---|---|
| A61K 31/546 | (2006.01) |
| A61K 9/00 | (2006.01) |
| A61K 9/14 | (2006.01) |
| A61K 9/10 | (2006.01) |
| A61K 31/192 | (2006.01) |
| A61K 47/24 | (2006.01) |
| A61K 47/26 | (2006.01) |
| A61K 47/44 | (2017.01) |
| A61K 45/06 | (2006.01) |

(52) U.S. Cl.
CPC .............. *A61K 9/0019* (2013.01); *A61K 9/10* (2013.01); *A61K 9/14* (2013.01); *A61K 31/192* (2013.01); *A61K 31/546* (2013.01); *A61K 45/06* (2013.01); *A61K 47/24* (2013.01); *A61K 47/26* (2013.01); *A61K 47/44* (2013.01)

(58) Field of Classification Search
CPC ...................................................... A61K 31/423
USPC .......................................... 514/206; 424/423
See application file for complete search history.

(56) References Cited

U.S. PATENT DOCUMENTS

| | | | |
|---|---|---|---|
| 4,614,741 A | 9/1986 | Dell et al. | |
| 4,902,683 A | 2/1990 | Amin et al. | |
| 5,736,151 A | 4/1998 | Foster et al. | |
| 2002/0058009 A1* | 5/2002 | Bartus ................. | A61K 9/0075 424/43 |
| 2003/0099601 A1 | 5/2003 | Gordon et al. | |
| 2004/0146537 A1 | 7/2004 | Radhakrishnan et al. | |

FOREIGN PATENT DOCUMENTS

| | | |
|---|---|---|
| WO | 98/041207 A1 | 9/1998 |
| WO | 2004/014390 A1 | 2/2004 |
| WO | 2010/059717 A2 | 5/2010 |

OTHER PUBLICATIONS

Translation of International Search Report of the International Searching Authority for Application No. PCT/IB2013/061141, dated Mar. 11, 2014 (3 pages).
Written Opinion of the International Searching Authority for Application No. PCT/IB2013/061141, dated Mar. 11, 2014 (8 pages).
Ingle et al., "The effect of aspirin upon the glycosuria of partially depancreatized rats in the presence and absence of the adrenal glands". Endocrinology, vol. 52, No. 4, 1953: pp. 403-406.

* cited by examiner

*Primary Examiner* — Johann R Richter
(74) *Attorney, Agent, or Firm* — Christensen O'Connor Johnson Kindness PLLC

(57) ABSTRACT

The invention relates to an oily composition of a non-steroidal anti-inflammatory agent (NSAIA) for parenteral administration with at least one micronized NSAIA, having an acid function and a biocompatible oily vehicle, such that said NSAIA is in the form of a free acid and said composition does not contain any added liquid agent that can solubilize said NSAIA. The invention also relates to the veterinary use thereof.

15 Claims, No Drawings

VETERINARY PHARMACEUTICAL COMPOSITIONS AND METHOD FOR THE PRODUCTION THEREOF

The present invention relates to the field of veterinary therapeutic chemistry and more particularly that of medicaments.

The subject thereof is novel veterinary pharmaceutical compositions with an anti-inflammatory action.

The subject thereof is specifically veterinary pharmaceutical compositions for parenteral administration containing, as active ingredient, a non-steroidal anti-inflammatory agent (NSAIA) in combination or as a mixture with an excipient or a vehicle which is suitable for veterinary use.

The present invention relates to an oily suspension for parenteral administration containing a non-steroidal anti-inflammatory agent (NSAIA) bearing an acid function, such as acetylsalicylic acid; arylacetic derivatives such as diclofenac, aceclofenac or sulindac; 2-arylpropionic acids such as ketoprofen, ibuprofen or naproxen, or indole derivatives such as indomethacin; more particularly, it is an oily suspension for parenteral administration comprising ketoprofen.

Ketoprofen, or 2-(3-benzoylphenyl)propionic acid, has been known as an anti-inflammatory non-steroidal drug since 1972. It has for a long time been sold in the form of immediate-action or sustained-action tablets and in ready-to-use injectable form.

It is commonly used for its analgesic, antipyretic and anti-inflammatory properties. It acts by inhibiting prostaglandin and leukotriene synthesis.

The injectable formulations currently sold use ketoprofen in soluble form; this is the case with the commercial products Ketofen® and Comforion®, in which a ketoprofen salt is formulated in an injectable aqueous solution. WO 99/27906 also describes sustained-release injectable solutions based on hydrogenated castor oil, in which the ketoprofen is solubilized.

Other documents, application US 2004/0146537 and patent U.S. Pat. No. 5,665,384, describe formulations of ketoprofen in oil, in particular in salt form, either its sodium salt, or a nitrogenous salt, such as the arginine, lysine or N-methylglucamine salt, but these are compositions intended for oral administration.

Treatments given to bovine, caprine, ovine and porcine livestock animals are mainly given via parenteral administration routes (including intramuscular, intradermal, intralesional, intra-articular or subcutaneous injection). In order to avoid carrying out several injections consecutively, it is preferable to provide the practitioner with a ketoprofen formulation which is compatible with injectable veterinary formulations, such as injectable oily suspensions of an antibiotic. The term "compatible" is intended to mean that the ketoprofen formulation can be mixed by the practitioner with other injectable veterinary compositions in the same syringe before giving the animal the injection or else that the ketoprofen formulation also comprises at least one other active ingredient such as an antibiotic.

International application WO 2010/059717 describes an injectable oily suspension of ceftiofur, in particular of ceftiofur hydrochloride, in a biocompatible oil also comprising ketoprofen and at least one preservative, one dispersing agent and one flocculation agent. However, such a formulation is of limited interest in that, because of the large number of ingredients that it comprises, it will be difficult to formulate therein high concentrations of active agents without increasing the volume of the biocompatible oil, and therefore the total volume of the composition to be injected, which can make its administration difficult. Moreover, the presence of numerous excipients increases the risk of incompatibility between the constituents and of toxicity in the animal for which it is intended.

Furthermore, in order to avoid interactions between excipients in a formulation, it is preferable to limit their amount and their diversity. Indeed, the combining of excipients can result in random behaviors of the suspension, for instance uncontrolled partial solubilizations of the active ingredient, resulting in different therapeutic actions or in gradient effects in the suspension which have the same consequences. Furthermore, the fewer constituents such as excipients there are, the lower the risk of incompatibility of the suspension when it is combined with other injectable formulations.

The Applicant has given itself the objective of developing an injectable NSAIA formulation which solves the following problems:
  this formulation must be such that it does not result in a delayed or sustained release of the NSAIA; and
  it must be able to be combined, by a practitioner, with other injectable oily veterinary formulations without risk.

Thus, in the context of its studies aimed at improving the formulation of ketoprofen for parenteral administration, the Applicant has noted that the use of the salified forms of NSAIAs bearing an acid function, such as their sodium salt or their lysine salt, results in a chemical instability of the NSAIA in the suspension. Conversely, NSAIAs bearing a free acid function can be advantageously formulated in suspension in an oil.

It has also observed that the use of an NSAIA in micronized form such that the particle size distribution is controlled and the particle size is small, unexpectedly improves the physical and chemical stability of the oily suspension and of the active agent.

It is known that the sedimentation rate of particles in suspension increases with the size of said particles and that the resuspension of the sedimented particles is easier the larger the size of these particles. It is also known that, while particles of small sizes have a tendency to sediment more slowly, the sediment formed with small particles comprises stronger particulate interactions and results in a phenomenon known as caking; in this case, resuspension is very difficult since it is necessary to break the interactions between the particles in order to obtain a homogeneous suspension.

Thus, in the present case, the stability of the oily suspension and the fact that the micronized NSAIA particles do not form a dense sediment which is difficult to resuspend appear to be notable.

It emerges from these studies that the Applicant has determined the particle size distribution of the micronized particles which is most suitable for suspending particles of an NSAIA, and more particularly ketoprofen, in an oily vehicle. The size of the micronized particles unexpectedly makes it possible to have both a high physical stability of the suspension and good resuspension, without being detrimental to good syringability and to the microbiological stability of the oily suspension.

The Applicant has thus demonstrated that such an oily suspension of a micronized NSAIA, in the absence of any excipient other than the oily vehicle:
  allows a rapid plasma release of the NSAIA, similar to that obtained after injection of an aqueous solution of ketoprofen salt, for instance Ketofen® or Comforion®;

is chemically stable;

is microbiologically stable; i.e. an oily suspension of ketoprofen which is sterile remains sterile even during several reuses after first opening (see example 3b);

exhibits very good physical stability allowing excellent resuspensions and syringability (see example 3c).

Thus, the present invention relates to an oily composition of a non-steroidal anti-inflammatory agent (NSAIA) for parenteral administration, comprising:

at least one NSAIA bearing an acid function; and a biocompatible oily vehicle, also denoted oil in the subsequent text, said composition being characterized in that:

said NSAIA is in free acid form;

preferably, said NSAIA is in suspension in said oily vehicle with particles having a size corresponding to the following specifications: a median diameter D (v, 0.5), 50% of the distribution being less than or equal to said median diameter value, of 35 µm, preferentially of 30 µm and even more preferentially of 25 µm, and a value D (v, 0.9), 90% of the distribution being less than or equal to said value, of 90 µm, preferentially of 85 µm and even more preferentially of 80 µm; and said composition contains no agent capable of solubilizing said NSAIA.

In the studies which have resulted in the development of the oily NSAIA composition according to the invention, the Applicant has noted that the formulation of the NSAIA in suspension in the oil (or oily vehicle) is essential for obtaining the advantageous properties of said composition, in particular for its stability but also for observing the desired (immediate-action) plasma profile.

Indeed, the use of compounds capable of solubilizing the NSAIA can result in formulations which exhibit a random therapeutic activity since, during the injection, the active ingredient will potentially return, at least partially, to a solid form, which will modify its distribution in the organism.

However, it should be emphasized that the formulation of a suspension poses difficulties and that an objective of the present invention is to develop a suspension which does not set and which is easily resuspended; more particularly, this suspension must be homogeneous and must not coagulate, and must not result in the formation of gelatinous masses, nor result in the formation of agglomerates, which are compact masses that are difficult to divide. Finally, the suspension must be chemically stable with respect to itself but also with respect to the other formulations which may be combined therewith.

Suspensions are dispersed systems in which an internal phase, which is a very finely divided solid (also subsequently referred to as particles), this phase is also denoted phase to be suspended, is uniformly distributed after mechanical stirring in an external phase known as suspending medium or vehicle. The internal phase is a uniform distribution of particles belonging to a specific size range.

The pharmaceutically acceptable vehicles most commonly used for parenteral suspensions are oils of natural or synthetic origin.

When it proves to be necessary, the maintaining of the solid particles in suspension in the suspending vehicle is improved by adding one or more suspending agents.

The stability of a suspension involves various factors; the maintaining of this stability is often complicated by the fact that the factors which affect the physical stability can also affect the chemical stability of the constituents of said suspension. This may be due to the fact that a suspension comprises matter in several physical states, solid and liquid.

During the life of the suspension, the dispersion of the solid matter in the liquid medium will change. This change results in the heterogeneous medium being subjected to various mechanisms that will both physically and chemically modify the suspension.

One means for preparing a satisfactory oily suspension is the use of a flocculated pharmaceutical suspension; this is a suspension in which the solid particles are capable of forming aggregates when the suspension is at rest, but which are easily resuspended by mechanical stirring.

The following definitions will be useful for differentiating three closely linked terms: flocculation, agglomeration and coagulation.

Flocculation refers to the formation of reversible aggregates, such as flakes, consisting of discrete particles held together by a network structure either by adsorption between the particles, or through the involvement of Van der Waals attractive forces to the detriment of repulsive forces.

The term "agglomeration" should be understood to mean that a large number of particles are tightly grouped together in a compact mass very difficult to dissociate.

Coagulation refers to a solid or semi-solid setting of particles in a liquid state, sometimes in the form of a fluid gel.

The main advantages of a flocculated suspension are the following:

1. the aggregates have a tendency to divide very easily by simple stirring or light shearing of the container containing the suspension, or even by simple passage through an orifice such as a needle for injection;

2. as opposed to deflocculated systems, flocculated suspensions will be able to sediment rapidly and be resuspended in the form of a homogeneous suspension very easily, even after a long period of storage at rest;

3. a flocculated suspension can be produced according to any method, even if this method requires the implementation of aseptic conditions for formulation of the constituents of the pharmaceutically acceptable vehicle.

Several methods make it possible to obtain flocculated pharmaceutical suspensions. The choice will depend on the properties of the active ingredient envisioned, but also on the desired suspension quality.

Authors have described methods for preparing such flocculated oily suspensions, for example by adding water (U.S. Pat. No. 5,736,151) or other organic solvents such as glycerol, propylene glycol, polyethylene glycol, or alcohols such as ethanol (U.S. Pat. No. 4,902,683 and WO 2004/014390); however, since these compounds are capable of solubilizing the free acid forms of NSAIAs bearing an acid function, they are preferentially to be avoided in the context of the present invention.

The Applicant has succeeded in preparing a stable oily NSAIA suspension with a uniform particle distribution by virtue of the choice of a particulate NSAIA particle size and by virtue of the uniformity of the size of these particles.

Advantageously and as previously set out, the size of the NSAIA particles corresponds to the following specifications: a value D (v, 0.5) less than or equal to 35 µm, preferentially less than or equal to 30 µm and even more preferentially less than or equal to 25 µm and a value D (v, 0.9) less than or equal to 90 µm, preferentially less than or equal to 85 µm and even more preferentially less than or equal to 80 µm. The size of the NSAIA particles can also be expressed as follows: it is between 1 and 100 µm, and more preferentially centered around 10 µm, 15 µm, 20 µm, 25 µm, 30 µm, 35 µm, 40 µm, 45 µm or 50 µm.

The following values for the size of the NSAIA particles in suspension in the oil will be preferred:

| D (v, 0.5)/D (v, 0.9) | D (v, 0.5)/D (v, 0.9) | D (v, 0.5)/D (v, 0.9) |
|---|---|---|
| 15 μm/90 μm | 15 μm/85 μm | 15 μm/80 μm |
| 20 μm/90 μm | 20 μm/85 μm | 20 μm/80 μm |
| 25 μm/90 μm | 25 μm/85 μm | 25 μm/80 μm |
| 30 μm/90 μm | 30 μm/85 μm | 30 μm/80 μm |
| 35 μm/90 μm | 35 μm/85 μm | 35 μm/80 μm |
| 40 μm/90 μm | 40 μm/85 μm | 40 μm/80 μm |
| 45 μm/90 μm | 45 μm/85 μm | 45 μm/80 μm |
| 50 μm/90 μm | 50 μm/85 μm | 50 μm/80 μm |

The composition according to the invention comprises between 1% and 30% by weight/volume (by weight relative to the volume of the final composition) of at least one non-steroidal anti-inflammatory agent (NSAIA) bearing an acid function; advantageously between 10% and 20% by weight/volume, and even more advantageously 15% by weight/volume.

Unless otherwise indicated, the concentrations mentioned in the subsequent text are expressed as percentage of the weight relative to the total volume of the composition (% by weight/volume).

This NSAIA content, in particular when said NSAIA is ketoprofen, makes it possible to obtain the best compromise between the therapeutic efficacy of the composition according to the invention and the volume to be injected, thus respecting, as far as possible, the well-being of the animal to be treated.

The NSAIAs bearing an acid function that are usable according to the invention can be chosen from ketoprofen, ibuprofen, naproxen, aceclofenac, sulindac, diclofenac, acetylsalicylic acid or indomethacin; ketoprofen is more particularly used.

The biocompatible oily vehicle is preferentially chosen from vegetable oils, for instance palm oil, corn oil, cottonseed oil, sunflower oil, peanut oil, olive oil, soybean oil, safflower oil, copra oil or sesame oil, or from semi-synthetic vegetable oils obtained by total esterification and/or hydrolysis and/or fractionation of natural vegetable oils, for instance fatty acid triglycerides derived from vegetable oils, such as triglycerides of caprylic, capric, linoleic or succinic acids (sold under the trade names Miglyol® 810, 812, 818, 820, 829), esters of propylene glycol and of a fatty acid, derived from vegetable oil, such as esters of propylene glycol and of caprylic and capric acid (sold under the trade name Miglyol® 840), and also mixtures thereof. Preferentially, the oily vehicle is cottonseed oil.

According to one particular embodiment of the invention, the oily NSAIA composition according to the invention contains no added liquid agent capable of solubilizing said non-steroidal anti-inflammatory compound in the oil; in particular, these agents excluded from the oily NSAIA composition according to the invention are: water, propylene glycol, glycerol, polyethylene glycol, $C_1$ to $C_6$ alcohols, such as ethanol, and also aromatic alcohols, i.e. compounds comprising a hydroxyl function directly bonded or bonded via an alkyl bond to an aromatic nucleus such as an optionally substituted phenyl nucleus, such as benzyl alcohol or phenylethyl alcohol, or an optionally substituted naphthyl nucleus.

According to one variant of this embodiment of the present invention, the oily NSAIA composition according to the invention contains no compound other than the NSAIA bearing an acid function and the biocompatible oily vehicle.

According to another particular embodiment of the invention, it is possible to add at least one wetting agent to the oily NSAIA composition.

The wetting agents that are usable according to the invention are chosen from: polyoxyethylenated hydrogenated castor oils, polyoxyethylenated castor oils, polyoxyethylenated hydrogenated vegetable oils, polyoxyethylenated hydrogenated vegetable oils, glyceryl monostearate, polyoxyethylenated castor oils, polyoxyethylenated fatty acid esters of sorbitan (sold under the trade names Montanox 20DF, 40DF, 60DF, 80 VG DF, 81, 85 VG DF), fatty acid esters of sorbitan (sold under the trade names Montane® 20, 40, 60, 65, 70, 80 VG PHA, 85 VG), soya or egg lecithin and its derivatives, for instance phosphatidylcholine (sold under the trade name Phospholipon® 90G), hydrogenated phosphatidylcholine (sold under the trade name Phospholipon® 80H, Phospholipon® 90H), lysophosphatidylcholine, hydrogenated lysophosphatidylcholine, and also combinations thereof.

The wetting agents are used at concentrations between 0.01% and 1% by weight/volume; advantageously between 0.05% and 0.25% by weight/volume, and even more advantageously at 0.20% by weight/volume. The wetting agent is preferentially sorbitan monooleate (Montane 80 VG PHA) and/or hydrogenated soya phosphatidylcholine (Phospholipon® 90H).

According to another embodiment of the present invention, the oily NSAIA composition according to the invention contains no compound other than the NSAIA bearing an acid function, the biocompatible oily vehicle and one or more wetting agents.

Advantageously, the compositions according to the invention can also comprise solid additional compounds such as antimicrobial agents, antioxidants, excipients and/or adjuvants which are physiologically acceptable. By way of examples of antioxidants, mention may be made, without limitation, of butylhydroxyanisole (BHA), butylhydroxytoluene (BHT) and mixtures thereof.

According to yet another preferred arrangement of the invention, the oily composition for parenteral administration according to the invention is used as a medicament for treatment of inflammation (anti-inflammatory action), of pain (analgesic action) and/or of fever (antipyretic action) in farm animals such as cattle or pigs, in particular as a supplement to a specific treatment with antibiotics. It can also advantageously be used as a medicament for pets, such as dogs and cats.

The oily NSAIA composition for parenteral administration according to the invention may be administered as sole treatment directly to the animal or may be combined extemporaneously with an oily antibiotic composition, either by mixing the compositions before the administration to the animal, or by sequential administration of each composition to the animal.

The oily NSAIA composition according to the invention proves to be particularly suitable for mixing and for administration with an oily antibiotic suspension such as an oily suspension of ceftiofur hydrochloride, for instance the commercial product Excenel® RTU, or an oily suspension of free-acid crystalline ceftiofur, for instance the commercial product Excede®, or an oily suspension of amoxicillin, for instance the commercial products Vetrimoxin®, Suramox® or Potencil® (an injectable suspension also containing Colistin in sulfate form). According to another subject thereof, the invention relates to an oily NSAIA composition for parenteral administration which comprises other medicinal active ingredients with a view to building the spectrum of activity of the composition, and of thus improving the therapeutic activity by simultaneously treating, in a single injection, several pathological conditions.

Thus, according to yet another arrangement, the present invention relates to an oily composition of a non-steroidal anti-inflammatory agent (NSAIA) and of an anti-infective agent for parenteral administration, comprising:

at least one NSAIA bearing an acid function;
at least one anti-infective agent, such as beta-lactam antibiotics, for instance benzylpenicillins or aminopenicillins or cephalosporins; and
a biocompatible oily vehicle;
said composition being characterized in that:
said NSAIA is in free acid form;
  said NSAIA and said anti-infective agent are in suspension in said oily vehicle with particles having a size corresponding to the following specifications: a median diameter D (v, 0.5), 50% of the distribution being less than or equal to said median diameter value, of 25 μm, preferentially of 20 μm, preferentially of 15 μm and even more preferentially of 10 μm, and a value D (v, 0.9), 90% of the distribution being less than or equal to said value, of 80 μm, preferentially of 75 μm, preferentially of 70 μm and even more preferentially of 65 μm; and
  said composition contains no agent capable of solubilizing said non-steroidal anti-inflammatory compound.

According to yet another preferred arrangement of the invention, the oily composition for parenteral administration according to the invention comprising at least one NSAIA bearing an acid function and at least one anti-infective agent is used as a medicament for treatment of infection and of inflammation (anti-inflammatory action), of pain (analgesic action) and/or of fever (antipyretic action) in farm animals such as cattle or pigs. It can also advantageously be used as a medicament for pets, such as dogs and cats.

The subject of the invention is also the oily composition for parenteral administration according to the invention comprising at least one NSAIA bearing an acid function and at least one anti-infective agent, such as beta-lactam antibiotics, for instance benzylpenicillins or aminopenicillins or cephalosporins, in a biocompatible oily vehicle; said composition being characterized in that:

said NSAIA is in free acid form;
  said NSAIA and said anti-infective agent are in suspension in said oily vehicle with particles having a size corresponding to the following specifications: a median diameter D (v, 0.5), 50% of the distribution being less than or equal to said median diameter value, of 25 μm, preferentially of 20 μm, preferentially of 15 μm and even more preferentially of 10 μm, and a value D (v, 0.9), 90% of the distribution being less than or equal to said value, of 80 μm, preferentially of 75 μm, preferentially of 70 μm and even more preferentially of 65 μm; and
  said composition contains no agent capable of solubilizing said non-steroidal anti-inflammatory compound;
for use in the treatment of infectious diseases of farm animals, such as cattle, members of the ovine race or members of the goat family, or pets such as dogs and cats.

A subject of the invention is also the use, for antipyretic and anti-inflammatory purposes, of the oily composition for parenteral administration according to the invention comprising at least one NSAIA bearing an acid function and at least one anti-infective agent, such as beta-lactam antibiotics, for instance benzylpenicillins or aminopenicillins or cephalosporins, in a biocompatible oily vehicle;

said composition being characterized in that:
said NSAIA is in free acid form;
  said NSAIA and said anti-infective agent are in suspension in said oily vehicle with particles having a size corresponding to the following specifications: a median diameter D (v, 0.5), 50% of the distribution being less than or equal to said median diameter value, of 25 μm, preferentially of 20 μm, preferentially of 15 μm and even more preferentially of 10 μm, and a value D (v, 0.9), 90% of the distribution being less than or equal to said value, of 80 μm, preferentially of 75 μm, preferentially of 70 μm and even more preferentially of 65 μm; and
  said composition contains no agent capable of solubilizing said non-steroidal anti-inflammatory compound.

In the same way as for the oily compositions of an NSAIA and of an anti-infective agent according to the invention, the biocompatible oily vehicle is chosen from vegetable oils, for instance palm oil, corn oil, cottonseed oil, sunflower oil, peanut oil, olive oil, soybean oil, safflower oil, copra oil or sesame oil, or from semi-synthetic vegetable oils obtained by total esterification and/or hydrolysis and/or fractionation of natural vegetable oils, for instance fatty acid triglycerides derived from vegetable oils, such as triglycerides of caprylic, capric, linoleic or succinic acids (sold under the trade names Miglyol® 810, 812, 818, 820, 829), esters of propylene glycol and of a fatty acid, derived from vegetable oil, such as esters of propylene glycol and of caprylic and capric acids (sold under the trade name Miglyol® 840), and also mixtures thereof. Preferentially, the oily vehicle is cottonseed oil.

The non-steroidal anti-inflammatory agent (NSAIA) is present at a concentration between 1% and 30% by weight/volume (by weight relative to the volume of the final composition), bearing an acid function; advantageously between 10% and 20% by weight/volume, and even more particularly 15% by weight/volume.

The NSAIAs bearing an acid function that are usable according to the invention can be chosen from ketoprofen, ibuprofen, naproxen, aceclofenac, sulindac, diclofenac, acetylsalicylic acid or indomethacin; ketoprofen is more particularly used.

As previously explained, it is advantageous to use NSAIA particles in suspension having a size corresponding to the following specifications: a median diameter D (v, 0.5), 50% of the distribution being less than or equal to said median diameter value, of 35 μm, preferentially of 30 μm and even more preferentially of 25 μm, and a value D (v, 0.9), 90% of the distribution being less than or equal to said value, of 90 μm, preferentially of 85 μm and even more preferentially of 80 μm. In other words, said NSAIA is in suspension in the oil with particles having a size between 1 and 100 μm, and more preferably centered around 10 μm, 15 μm, 20 μm, 25 μm, 30 μm, 35 μm, 40 μm, 45 μm or 50 μm.

The following values for the size of the NSAIA particles in suspension in the oil will be preferred:

| D (v, 0.5)/D (v, 0.9) | D (v, 0.5)/D (v, 0.9) | D (v, 0.5)/D (v, 0.9) |
| --- | --- | --- |
| 15 μm/90 μm | 15 μm/85 μm | 15 μm/80 μm |
| 20 μm/90 μm | 20 μm/85 μm | 20 μm/80 μm |
| 25 μm/90 μm | 25 μm/85 μm | 25 μm/80 μm |
| 30 μm/90 μm | 30 μm/85 μm | 30 μm/80 μm |
| 35 μm/90 μm | 35 μm/85 μm | 35 μm/80 μm |
| 40 μm/90 μm | 40 μm/85 μm | 40 μm/80 μm |
| 45 μm/90 μm | 45 μm/85 μm | 45 μm/80 μm |
| 50 μm/90 μm | 50 μm/85 μm | 50 μm/80 μm |

According to one advantageous embodiment of said oil compositions of an NSAIA and of an anti-infective agent for parenteral administration of the invention, the anti-infective agent is an antibiotic of the beta-lactam family, preferably a cephalosporin and more particularly ceftiofur hydrochloride.

The compositions according to the invention comprise between 1% and 20% by weight/volume of anti-infective agent, advantageously between 1% and 10% by weight/volume, and more particularly 5% by weight/volume.

In order to ensure the stability of the suspension, it is important for said anti-infective agent, which is also in suspension in the biocompatible oily vehicle, to be in the form of a particle having a size close to that of the NSAIA particles, i.e. a size corresponding to the following specifications: a median diameter D (v, 0.5), 50% of the distribution being less than or equal to said median diameter value, of 15 μm, preferentially of 10 μm and even more preferentially of 5 μm, and a value D (v, 0.9) 90% of the distribution being less than or equal to said value, of 65 μm, preferentially of 50 μm and even more preferentially of 35 μm. In other words, said anti-infective agent is in suspension in the oil with particles having an average size between 1 and 100 μm, preferentially centered between 2 and 20 μm and more particularly centered around 1 μm, 2 μm, 3 μm, 4 μm, 5 μm, 6 μm, 7 μm or 8 μm.

More particularly, the compositions according to the invention are such that the ratio of the average size of the anti-infective agent particles relative to the average size of the NSAIA particles is between 1:3 and 1:30, preferentially 1:5 and 1:15 and even more preferentially between 1:5 and 1:8.

According to one particular embodiment of the invention, the oily composition of an NSAIA and of an anti-infective agent according to the invention contains no agent capable of solubilizing the two active ingredients in the oil; in particular, these agents excluded from the oily NSAIA composition according to the invention are: water, propylene glycol, glycerol, polyethylene glycol, $C_1$ to $C_6$ alcohols such as ethanol, and also aromatic alcohols, i.e. compounds comprising a hydroxyl function directly bonded or bonded via an alkyl bond to an aromatic nucleus, such as a phenyl nucleus, for instance benzyl alcohol or phenylethyl alcohol, or an optionally substituted naphthyl nucleus.

According to one particularly preferred embodiment, the oily composition of an NSAIA and of an anti-infective agent according to the invention does not contain benzyl alcohol.

According to another particular embodiment of the invention, it is possible to add at least one wetting agent to the oily composition of an NSAIA and of an anti-infective agent.

The wetting agents that are usable according to the invention are chosen from: polyoxyethylenated hydrogenated castor oils, polyoxyethylenated castor oils, polyoxyethylenated hydrogenated vegetable oils, polyoxyethylenated hydrogenated vegetable oils, glyceryl monostearate, polyoxyethylenated fatty acid esters of sorbitan (sold under the trade names Montanox 20DF, 40DF, 60DF, 80 VG DF, 81, 85 VG DF), fatty acid esters of sorbitan (sold under the trade names Montane® 20, 40, 60, 65, 70, 80 VG PHA, 85 VG), soya or egg lecithin and its derivatives, for instance phosphatidylcholine (sold under the trade name Phospholipon® 90G), hydrogenated phosphatidylcholine (sold under the trade name Phospholipon® 80H, Phospholipon® 90H), lysophosphatidylcholine, hydrogenated lysophosphatidylcholine, and combinations thereof.

The wetting agents are used at concentrations between 0.01% and 1% by weight/volume; advantageously between 0.05% and 0.25% by weight/volume, and even more advantageously at 0.2% by weight/volume. The wetting agent is preferentially sorbitan monooleate (Montane 80 VG PHA) and/or hydrogenated soya phosphatidylcholine (Phospholipon® 90H).

The impact of ceftiofur hydrochloride in the formulation according to the invention on plasma ketoprofen concentrations was evaluated by comparing the ketoprofen kinetics after administration of the oily composition according to the invention containing ceftiofur hydrochloride and ketoprofen and a composition of ceftiofur hydrochloride alone. It was observed, unexpectedly, that the ceftiofur hydrochloride increased the bioavailability of the ketoprofen. From a clinical point of view, the anti-inflammatory and antipyretic activities of the combination were shown to be comparable to those of the reference product (Ketofen®, Merial), without any additional safety problem.

According to one particular embodiment, the present invention relates to one of the following compositions:

| Name | % w/V | amount for 1 ml |
|---|---|---|
| Active agent | | |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| cottonseed oil | up to 100% | up to 1 ml |
| Active agents | | |
| Ceftiofur (in hydrochloride form) | 5% | 50 mg |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| cottonseed oil | up to 100% | up to 1 ml |

The oily compositions for parenteral administration are prepared according to a method comprising the following steps:

i) heating the biocompatible oily vehicle, ii) optionally, adding the suspending agent or the wetting agent, iii) cooling with stirring, iv) optionally, adding the second suspending agent or the wetting agent, v) adding the non-steroidal anti-inflammatory agent bearing an acid function, vi) optionally, adding the anti-infective agent, vii) mixing with stirring until a homogeneous suspension is obtained, viii) dispensing into the primary packaging, ix) sterilizing by gamma-irradiation at a minimum of 25 kGy.

The invention will be understood more clearly on reading the additional description which follows and which refers to exemplary embodiments of oily compositions for parenteral administration in accordance with the invention, and also demonstrations of the particular properties thereof. It should be understood, however, that these examples are given merely by way of illustration of the invention and in no way constitute a limitation thereof.

EXAMPLE 1—OILY COMPOSITION FOR PARENTERAL ADMINISTRATION CONTAINING 10% BY WEIGHT/VOLUME OF KETOPROFEN

| Formula | Amount by w/V |
|---|---|
| Ketoprofen | 10.0% |
| Cottonseed oil qs | 100.0% |

The ketoprofen is dispersed with stirring in the cottonseed oil until a homogeneous suspension is obtained.

The suspension is then dispensed into glass bottles and then the bottles are sterilized by gamma-irradiation at approximately 25 kGy.

EXAMPLE 2—OILY COMPOSITION FOR PARENTERAL ADMINISTRATION COMPRISING 15% BY WEIGHT/VOLUME OF KETOPROFEN

The composition having the following formula is prepared:

| Name | % w/V | amount for 1 ml |
|---|---|---|
| Active agent | | |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| cottonseed oil | up to 100% | up to 1 ml |

All of the cottonseed oil is heated to 100° C. with slow stirring. When the temperature has been reached, Phospholipon 90 H is dispersed with stirring; the stirring is maintained until the Phospholipon 90 H has completely melted.

The preparation is cooled to 25° C. and then Montane 80 VG PHA is introduced.

The ketoprofen is then introduced into the mixture with stirring, with the stirring being maintained for approximately 40 minutes while making sure that the temperature remains at approximately 20° C.

The suspension is dispensed into glass bottles. The bottles are sterilized by gamma-irradiation at approximately 25 kGy.

EXAMPLE 3—STUDY OF THE CHEMICAL AND PHYSICAL PARAMETERS OF THE OILY SUSPENSION OF EXAMPLE 2

The following parameters were evaluated and studied for the oily ketoprofen suspension obtained according to the method described in example 2.

a) Particle Size Study

The size of the ketoprofen particles was measured using a Laser Mastersizer 2000 particle sizer. The particle size distribution is:

| | D (v; 0.1) | D (v; 0.5) | D (v; 0.9) |
|---|---|---|---|
| Ketoprofen (Batch n° 10126) | ≤2.4 µm | ≤12.7 µm | ≤44.8 µm |

D (v, 0.1) is the value of the diameter for which 10% of the distribution is less than or equal to said value;
D (v, 0.5) is the value of the median diameter for which 50% of the distribution is less than or equal to said value, and
D (v, 0.9) is the value of the diameter for which 90% of the distribution is less than or equal to said value.

b) Sterility Study at time zero after irradiation

The study is carried out by membrane filtration in accordance with the pharmaceutical regulation in force after validation.

The product of example 2 proved to be sterile.

after several uses

One unit of this product can be used to treat an animal or several animals after a single or several withdrawals of the oily composition at the same time or at different times which can be spread out over several months. A simulation of this veterinary practice was carried out on several 250 ml bottles. For this, at time zero ($t_0$), at time 1 month ($t_{1\ month}$), at time 2 months ($t_{2\ months}$), and at time 3 months ($t_{3\ months}$), a 50 ml sample was taken per flask using a syringe fitted with a needle, the whole assembly being sterile, as the vet would do. Throughout the study, the bottles were stored in the usual manner for this type of product. The sterility study as presented above after irradiation was carried out for each of the samples taken at the various times. No contamination was noted, thereby showing that the composition remained sterile for at least 3 months.

c) Study of Resuspension and of Resyringability resuspension

A centrifugation-resuspension test was carried out according to the following technique: 16 g of oily suspension of suspension are introduced into a 25 ml tube. The tube is placed in a centrifuge at 5000 revolutions/min at 25° C. for 15 minutes. The sediment volume and the centrifugation pellet resuspension time are determined. After the determination of the sedimentation percentage (ratio between the height of the pellet and the total height of the suspension in the tube), the resuspension time is investigated through successive manual shaking of the tube for 5 seconds. The resuspension is considered to be obtained when there is no longer any product stuck to the bottom of the tube.

The oily suspension containing 15% by weight/volume of ketoprofen according to the invention described in example 2, which is a suspension having the same formula as the suspension according to the invention but containing in addition 1% by weight/volume of benzyl alcohol as secondary solvent facilitating the resuspension, and an oily suspension containing 15% by weight/volume of commercial amoxicillin (Suramox®), taken as reference since animal health professionals acknowledge that it resuspends completely, were compared:

| | Oily suspension of Ketoprofen according to example 2 (Batch 10126) | Oily suspension of Ketoprofen containing 1% of benzyl alcohol (Batch 11165) | Oily suspension of amoxicillin (Batch 32Y3) |
|---|---|---|---|
| Sedimentation | 79.2% | 78.3% | 74.7% |
| Resuspension time | 50 sec | 70 sec | 40 sec |

While the oily suspension of ketoprofen according to the invention is equivalent to a reference suspension of the market, it is no longer the same as the latter when a solvent is added to facilitate said resuspension.

Syringability

The syringability test, which test makes it possible to evaluate the ability to fill and empty a syringe through a needle, i.e. the forces to be applied to the plunger of a syringe fitted with a 14G needle in order to draw up 10 ml of suspension and to discharge these same 10 milliliters from the syringe through the 14G needle, was carried out on the oily suspension containing 15% (w/V) of ketoprofen according to the invention described in example 2, which is a suspension having the same formula as the suspension according to the invention but containing in addition 1% (w/V) of benzyl alcohol as secondary solvent facilitating the resuspension, an oily suspension containing 15% (w/V) of commercial amoxicillin (Suramox®), taken as reference since animal health professionals acknowledge that it can be satisfactorily sampled and injected, and a commercial aqueous solution containing 10% (w/V) of ketoprofen and 1% of benzyl alcohol (Ketofen®):

|  | Oily suspension of Ketoprofen according to the invention (Batch 10126) | Oily suspension of Ketoprofen containing 1% of benzyl alcohol (Batch 11165) | Oily suspension of Amoxicillin (Batch 32Y3) | Aqueous solution of Ketoprofen containing 1% of benzyl alcohol (Batch WO91101F) |
|---|---|---|---|---|
| Force to draw up 10 ml | 6.5N | 5.5N | 8.4N | 11.8N |
| Force to discharge 10 ml | 8.4N | 7.9N | 34.1N | 13.7N |

With regard to syringability, the oily suspension of ketoprofen according to the invention is equivalent to the same suspension containing 1% of fluidizing solvent; it proves to be greater than a reference of the market and even than an aqueous solution of the same active ingredient known to be easily injected.

d) Ketoprofen Pharmacokinetics Study

A study of the pharmacokinetics of the oily composition in accordance with the invention of ketoprofen was carried out in cattle by intramuscular parenteral administration.

Each of the six animals of the group, weighing between 239 and 312 kg, the group being composed of cattle of the Croisé, Limousine and Blonde d'Aquitaine breed and both sexes, received 3 mg of ketoprofen per kg of live weight of the oily composition described in example 2, intramuscularly.

10 ml blood samples were taken at each sampling time in lithium heparin tubes. The samples were taken at the following times: before the treatment and at 5 min, 10 min, 20 min, 30 min, 40 min, 60 min and at 1.5 h, 2 h, 3 h, 4 h, 6 h, 8 h, 12 h and 24 h after the treatment with the oily composition in accordance with the invention.

The sample analysis was carried out according to the chromatographic techniques, HPLC with UV detection, well known to those skilled in the art.

The pharmacokinetic parameters obtained, i.e. the Cmax (maximum plasma concentration), the Tmax (time to reach the maximum plasma concentration) and the apparent half-life time $t_{half}$ are represented below.

|  | $C_{max}$ (ng · ml$^{-1}$) | Tmax (h) | Apparent $t_{half}$ (h) |
|---|---|---|---|
| Example 2 | 6164 ± 2031 | 0.72 ± 0.23 | 2.42 |
| Comforion ® data from the literature aqueous formulation containing: | 9700 | 0.5 | 2.5 |
| Ketoprofen (100 mg/ml) Arginine citric acid monohydrate benzyl alcohol | | | |

These results show that the oily composition of example 2, in accordance with the invention, compared with the data from the literature (ref: Summary of Product Characteristics—http://www.hevra.org/vmri_spc/spc.asp?Product_Identifier=FI/V/0101/001) is similar to an aqueous solution from the pharmacokinetic point of view.

e) Extemporaneous Combination with Excenel® RTU

The oily composition of example 1 is mixed with Excenel® RTU at equal volume. Excenel® RTU is an oily antibiotic suspension sold in the veterinary field. Perfect compatibility between the two oily vehicles is observed. No demixing is observed, nor any emulsion, as will occur if water was present. After stirring, the suspension formed is perfectly homogeneous and exhibits no viscous mass or agglomerate. The suspension passes perfectly through an orifice such as a needle for injection.

EXAMPLE 4—OILY COMPOSITION FOR PARENTERAL ADMINISTRATION CONTAINING 15% BY W/V OF KETOPROFEN AND 5% BY W/V OF CEFTIOFUR

The composition having the following formula is prepared:

| Name | % w/V | amount for 1 ml |
|---|---|---|
| Active agents | | |
| Ceftiofur (in hydrochloride form) | 5% | 50 mg |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| cottonseed oil | Up to 100% | up to 1 ml |

All of the cottonseed oil is heated to 100° C. with slow stirring. When the temperature has been reached, Phospholipon 90 H is dispersed with stirring. The stirring is maintained until the Phospholipon 90 H has completely melted.

The preparation is allowed to cool to 25° C. and Montane 80 VG PHA is introduced. The Ceftiofur hydrochloride is introduced with stirring, with the stirring being maintained for approximately 20 minutes while making sure that the temperature remains at approximately 20° C. The ketoprofen is introduced with stirring, with the stirring being maintained for approximately 40 minutes while making sure that the temperature remains at approximately 20° C. The suspension is dispensed into glass bottles. The bottles are sterilized by gamma-irradiation at approximately 25 kGy.

EXAMPLE 5—STUDY OF THE CHEMICAL AND PHYSICAL PARAMETERS OF THE OILY SUSPENSION OF EXAMPLE 4

The following parameters were evaluated and studied for the oily suspension of ketoprofen and Ceftiofur (batch 10092), obtained according to the method described in example 4.

a) Particle Size Study

The size of the ketoprofen/Ceftiofur particles was measured using a Laser Mastersizer 2000 particle sizer. The particle size distribution is:

|  | D (v; 0.1) | D (v; 0.5) | D (v; 0.9) |
|---|---|---|---|
| Batch n° MER 10092 | ≤1.5 μm | ≤5.4 μm | ≤22.2 μm | b) Sterility Study at time zero after irradiation

The study is carried out by membrane filtration in accordance with the pharmaceutical regulations in force after validation.

The product of example 4 proved to be sterile.

after several uses

One unit of this product can be used to treat an animal or several animals after a single or several withdrawals of the oily composition at the same time or at different times which can be spread out over several months. A simulation of this veterinary practice was carried out on several 250 ml bottles. For this, at time zero ($t_0$), at time 1 month ($t_{1\ month}$), at time 2 months ($t_{2\ months}$) and at time 3 months ($T_{3\ months}$), a 50 ml sample was taken per bottle using a syringe fitted with a needle, the whole assembly being sterile, as the vet would do. Throughout the study, the bottles were stored in the usual manner for this type of product. The sterility study as presented above after irradiation was carried out for each of the samples taken at the various times. No contamination was noted, thereby showing that the composition remained sterile for at least 3 months.

c) Syringability Study

The syringability test, which test makes it possible to evaluate the ability to fill and empty a syringe through a needle, i.e. the forces to be applied to the plunger of a syringe fitted with a 14G needle in order to draw up 10 ml of suspension and to discharge these same 10 milliliters from the syringe through the 14G needle, was carried out on the oily suspension containing 15% by weight/volume of ketoprofen and 5% by weight/volume of Ceftiofur according to the invention described in example 4, and an oily suspension containing 15% by weight/volume of commercial amoxicillin (Suramox®), taken as reference since animal health professionals acknowledge that it can be satisfactorily sampled and injected, and a commercial aqueous solution containing 10% (w/V) of ketoprofen and 1% of benzyl alcohol (Ketofen®):

|  | Oily suspension of ketoprofen/Ceftiofur according to example 4 (Batch 10092) | Oily suspension of amoxicillin (Batch 32Y3) | Aqueous solution of ketoprofen containing 1% of benzyl alcohol (Batch WO91101) |
|---|---|---|---|
| Force to draw up 10 ml | 5.8N | 8.4N | 11.8N |
| Force to discharge 10 ml | 8.1N | 34.1N | 13.7N |

The oily suspension of ketoprofen/Ceftiofur according to the invention is much better than the reference of the market and even than an aqueous solution of ketoprofen known to be easily injected.

d) Study of the Pharmacokinetics of Ketoprofen in the Presence or Absence of Ceftiofur (Comparison of Examples 2 and 4)

The pharmacokinetics study was carried out in cattle, intramuscularly, for the oily compositions in accordance with the invention described in examples 2 and 4. Each of the animals of each of the two groups of six cattle, weighing between 239 and 312 kg, the two groups being composed of cattle of the Croise, Limousine and Blonde d'Aquitaine breed and of both sexes, received:

3 mg of ketoprofen per kg of live weight of the oily composition described in example 2, for the first group, 3 mg of ketoprofen and 1 mg of ceftiofur per kg of live weight of the oily composition described in example 4, for the second group.

10 ml blood samples were taken at each sampling time in lithium heparin tubes. The samples were taken at the following times: before the treatment and at 5 min, 10 min, 20 min, 30 min, 40 min, 60 min and at 1.5 h, 2 h, 3 h, 4 h, 6 h, 8 h, 12 h and 24 h after the treatment with the oily composition in accordance with the invention.

The analysis of the samples was carried out according to the chromatographic techniques, HPLC with UV detection, well known to those skilled in the art.

The pharmacokinetic parameters obtained, i.e. the Cmax (maximum plasma concentration), the AUClast (area under the curve until the last concentration measured) and the apparent half-life time $t_{half}$, are represented below.

For Ketoprofen:

| Group treated with | $C_{max}$ (ng · mL$^{-1}$) | AUClast (ng · h · mL$^{-1}$) | Apparent $t_{half}{}^a$ (h) |
|---|---|---|---|
| Example 2 | 6164 ± 2031 | 19571 ± 3705 | 2.42 |
| Example 4 | 5546 ± 1583 | 27186 ± 4680 | 3.75 |

$^a$harmonic mean

The data in the table show that the addition of another active agent slightly modified the bioavailability of the ketoprofen (as reflected by the AUClast).

EXAMPLE 6—CLINICAL STUDY OF THE OILY SUSPENSION OF EXAMPLE 4

This comparative study of the antipyretic and anti-inflammatory effects of ketoprofen was carried out in cattle.

Each of the animals of each of the three groups of eight cattle, weighing between 239 and 312 kg, the three groups being composed of cattle of the Croise, Limousine and Blonde d'Aquitaine breed and of both sexes, received by intramuscular injection:
- 3 mg of ketoprofen per kg of live weight of the oily composition described in example 4, for the first group,
- 3 mg of ketoprofen per kg of live weight of Ketofen®, an aqueous solution, for the second group, and
- a saline solution as a negative control.

One hour before the treatment with one of the three compositions, each of the cattle received, intravenously, a solution of *Escherichia coli* (055:B5) endotoxins in a proportion of $40.6\pm0.9$ ng·kg$^{-1}$.

The parameters, which were the rectal temperature and the thromboxane B2 level, were monitored for 10 hours and show that the antipyretic and anti-inflammatory effects of the oily suspension in accordance with the invention are not different than those of the aqueous solution of ketoprofen.

EXAMPLE 7—OILY COMPOSITION FOR PARENTERAL ADMINISTRATION CONTAINING 10% BY WEIGHT/VOLUME OF KETOPROFEN AND 5% BY WEIGHT/VOLUME OF AMOXICILLIN

| Formula | Amount by w/V |
|---|---|
| Ketoprofen | 10.0% |
| Anhydrous amoxicillin | 5.0% |
| Stearic acid | 1.5% |
| Aluminum stearate | 1.3% |
| Cottonseed oil qs | 100.0% |

EXAMPLE 8—OILY COMPOSITION FOR PARENTERAL ADMINISTRATION CONTAINING 10% BY WEIGHT/VOLUME OF IBUPROFEN AND 4% BY WEIGHT/VOLUME OF CEPHALEXIN

| Formula | Amount by w/V |
|---|---|
| Ibuprofen | 10.0% |
| Cephalexin (in monohydrate form) | 4.0% |
| Mygliol 840 qs | 100.0% |

The invention claimed is:

1. An oily composition of a non-steroidal anti-inflammatory agent (NSAIA) for parenteral administration, comprising:
   a) at least one NSAIA bearing an acid function; and
   b) a biocompatible oily vehicle; wherein
      i) said NSAIA is in free acid form;
      ii) said NSAIA corresponds to the following specifications: a median diameter D (v,0.5), 50% of the distribution being less than or equal to said median diameter value of 35 μm, and a value, D (v,0.9), 90% of the distribution being less than or equal to said value of 90 μm; and
      iii) said composition contains no added liquid agent capable of solubilizing said NSAIA, wherein said added liquid agent capable of solubilizing said non-steroidal anti-inflammatory compound is chosen from water, propylene glycol, glycerol, polyethylene glycol, C1 to C6 alcohols, benzyl alcohol and the other aromatic alcohols;
   and wherein said composition is a flocculated suspension.

2. The composition of claim 1, comprising between 1% and 30% by weight/volume of at least one non-steroidal anti-inflammatory agent bearing an acid function.

3. The composition of claim 2, wherein said non-steroidal anti-inflammatory agent bearing an acid function is ketoprofen.

4. The composition of claim 3, wherein the size of the ketoprofen particles in suspension in said oily vehicle corresponds to the following specifications: a median diameter D (v,0.5), 50% of the distribution being less than or equal to said median diameter value of 25 μm, and a value D (v,0.9), 90% of the distribution being less than or equal to said value of 80 μm.

5. The composition of claim 1, wherein said oily vehicle is cottonseed oil.

6. The composition of claim 1, further comprising at least one wetting agent which is chosen from: glyceryl monostearate, polyoxyethylenated castor oils, polyoxyethylenated fatty acid esters of sorbitan, fatty acid esters of sorbitan, soya or egg lecithin and its derivatives, for instance phosphatidylcholine, hydrogenated phosphatidylcholine, lysophosphatidylcholine, hydrogenated lysophosphatidylcholine, and combinations thereof.

7. The composition of claim 6, wherein said wetting agent(s) is/are present at concentrations between 0.01% and 1% by weight/volume.

8. The composition of claim 6, wherein said wetting agent is sorbitan monooleate and/or hydrogenated soya phosphatidylcholine.

9. The composition of claim 1, wherein it has the following:

| Name | % w/V | amount for 1 ml |
|---|---|---|
| Active agent | | |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| Cottonseed oil | up to 100% | up to 1 ml. |

10. The composition of claim 1, further comprising at least one anti-infective agent in suspension in said oily vehicle.

11. The composition of claim 10, wherein said anti-infective agent IS a beta-lactam antibiotic chosen from benzylpenicillins, aminopenicillins or cephalosporins.

12. The composition of claim 11, wherein the anti-infective agent is ceftiofur hydrochloride.

13. The composition of claim 10, wherein the size of the anti-infective agent particles in suspension in said oily vehicle corresponds to the following specifications: a median diameter D (v,0.5), 50% of the distribution being less than or equal to said median diameter value of 15 μm, and a value D (v,0.9), 90% of the distribution being less than or equal to said value of 65 μm.

14. The composition of claim 10, wherein said composition comprises between 1% and 20% by weight/volume of anti-infective agent.

15. The composition of claim 10, wherein it has the following:

| Name | % w/V | amount for 1 ml |
|---|---|---|
| Active agents | | |
| Ceftiofur (in hydrochloride form) | 5% | 50 mg |
| Ketoprofen | 15% | 150 mg |
| Excipients | | |
| Sorbitan oleate | 0.15% | 1.5 mg |
| Hydrogenated phosphatidylcholine, grade 90 | 0.05% | 0.5 mg |
| Cottonseed oil | Up to 100% | up to 1 ml. |

* * * * *